(12) United States Patent  (10) Patent No.: US 6,638,685 B2
Maeda et al.  (45) Date of Patent: Oct. 28, 2003

(54) PHOTOACID GENERATOR CONTAINING TWO KINDS OF SULFONIUM SALT COMPOUND, CHEMICALLY AMPLIFIED RESIST CONTAINING THE SAME AND PATTERN TRANSFER METHOD

(75) Inventors: Katsumi Maeda, Tokyo (JP); Shigeyuki Iwasa, Tokyo (JP); Kaichiro Nakano, Tokyo (JP); Etsuo Hasegawa, Tokyo (JP)

(73) Assignee: NEC Corporation, Tokyo (JP)

( * ) Notice: Subject to any disclaimer, the term of this patent is extended or adjusted under 35 U.S.C. 154(b) by 134 days.

(21) Appl. No.: 09/987,424

(22) Filed: Nov. 14, 2001

(65) Prior Publication Data

US 2002/0182535 A1 Dec. 5, 2002

(30) Foreign Application Priority Data

Nov. 15, 2000 (JP) .......................... 2000-347900

(51) Int. Cl.$^7$ .......................... G03C 7/038; G03C 7/40
(52) U.S. Cl. .................... 430/270.1; 430/325; 430/330; 549/399; 568/42
(58) Field of Search ............... 430/270.1, 330, 430/325; 549/399; 568/42

(56) References Cited

FOREIGN PATENT DOCUMENTS

| DE | 10054550 A1 | * | 5/2001 | ......... C07C/323/22 |
|---|---|---|---|---|
| EP | 001267210 A2 | * | 6/2002 | ........... G03F/7/004 |
| JP | 2-27660 | | 1/1990 | |
| JP | 9-73173 | | 3/1997 | |
| JP | 10-111569 | | 4/1998 | |
| JP | 10-218941 | | 8/1998 | |
| JP | 2856116 | | 11/1998 | |
| JP | 11-295894 | | 10/1999 | |
| JP | 11-305444 | | 11/1999 | |
| JP | 2000-26446 | | 1/2000 | |
| JP | 2003005374 | * | 1/2003 | ........... G03F/7/039 |

OTHER PUBLICATIONS

Hiroshi Ito and C. Grant Willson, "Applications of Photo-initiators to the Design of Resists for Semiconductor Manufacturing", American Chemical Society Symposium Series Vol 242, pp. 11–23.

(List continued on next page.)

*Primary Examiner*—Janet Baxter
*Assistant Examiner*—Amanda C. Walke
(74) *Attorney, Agent, or Firm*—McGinn & Gibb, PLCC

(57) ABSTRACT

A chemically amplified photo-resist contains a photoacid generator for changing the solubility of resin after exposure to 130–220 nanometer wavelength light, and the photoacid generator contains two kinds of sulfonium salt compound expressed by general formulae [1] and [2]

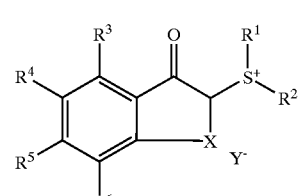

(1)

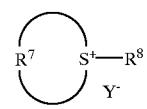

(2)

so that the chemically amplified photo-resist is improved in resolution, sensitivity and smoothness on side surfaces of a transferred pattern.

18 Claims, 2 Drawing Sheets

OTHER PUBLICATIONS

Donald C. Hofer, et al., "193 nm Photoresist R&D: The Risk & Challenge", Journal of Photopolymer Science and Technology vol. 9, No. 3 (1996), pp. 387–397.

Naitoh et al., The 8th Lecytres on Photo–Reactive Materials for Electric Devices,(1999), pp. 16–18.

Koji Nozaki and Ei Yano, "New Protective Groups in Alicyclic Methacrylate Polymers for 193–nm Resists", Journal of Photopolymer Science and Technology, vol. 10, No. 4, pp. 545–550.

Journal of the Organic Chemistry vol. 43, No. 15, 1978, "A New Preparation of Triarylsullfonium and –selenonium Salts via the Copper (II)—Catalyzed Arylation of Sulfides and Selenides with Diaryliodonium Salts", James V. Crivello and Julia H. Lam, pp. 3055–3058.

Yamachika et al., "Improvement of Post–Exposure Delay Stability in Alicyclic ArF Excimer Photoresists", Journal of Photopolymer Science and Technology vol. 12, No. 4 (1999), pp. 553–559.

Jung et al., "A Novel Alicyclic Polymers for 193nm Single Layer Resist Materials", Journal of Photopolymer Science and Technology vol. 11, No. 3 (1998), pp. 481–488.

Houlihan et al., "A Commercially Viable 193 nm Single Layer Resist Platform", Journal of Photopolymer Science and Technology vol. 10, No. 3 (1997), pp. 511–520.

Allen, et al., "Platform–Dependent Properties of 193nm Single Layer Resists", Journal of Photopolymer Science and Technology vol. 11, No. 3 (1998), pp. 475–480.

Iwasa, et al. "Chemically Amplified Negative Resists Based on Alicyclic Acrylate Polymers for 193–nm Lithography", Journal of Photopolymer Science and Technology vol. 12, No. 3 (1999), pp. 487–492.

* cited by examiner

PHOTOACID GENERATOR CONTAINING TWO KINDS OF SULFONIUM SALT COMPOUND, CHEMICALLY AMPLIFIED RESIST CONTAINING THE SAME AND PATTERN TRANSFER METHOD

FIELD OF THE INVENTION

This invention relates to a photo-lithography and, more particularly, to a photoacid generator, a chemically amplified resist containing the photoacid generator and a pattern transfer method.

DESCRIPTION OF THE RELATED ART

A dynamic random access memory is a typical example of the ultra large scale integration. Growing research and development efforts are being made for the ultra large scale integration which will be improved in integration density and operation speed. One of the approaches for a high-speed high-integration density semiconductor integrated circuit device is to scale down the circuit components. The semiconductor integrated circuit devices are usually fabricated through epitaxial growing techniques and pattern transfer technologies. Submicron-order pattern transfer technologies are required for the miniature circuit components.

A photo-mask is exposed to light. Then, a pattern is transferred from a photo-mask to a photo-resist layer so as to form a latent image in the photo-resist layer. When the latent image is developed, the photo-resist layer is patterned into a photo-resist mask with a submicron-order pattern. The shorter the wavelength, the finer the transferred pattern. In general, the resolution R in an optical system is expressed by Rayleigh's equation, i.e., $R = k \cdot \lambda / NA$ where k is a process factor, $\lambda$ is the wavelength of the light and NA is the numerical aperture. The resolution is a function of the wavelength. It is understood from the Rayleigh's equation that a miniature pattern is obtainable from an optical system at a small resolution. A short wavelength light is required for the optical system at a small resolution.

0.22 micron line-and-space patterns are used in a 256 mega-bit dynamic random access memory device. The 0.22 micron line-and-space pattern is transferred through a KrF excimer laser light. The wavelength of the KrF excimer laser light is 248 nanometers. Dynamic random access memory devices in the next generation, i.e., 1 mega-bit dynamic random access memory devices are to be fabricated by using 0.15 micron patterns or less. The wave-length of the KrF excimer laser light is too long to transfer the 0.15 micron patterns to photo-resist layers. ArF excimer laser light and $F_2$ excimer laser light have the wavelengths shorter that that of the KrF excimer laser light. The wavelength of ArF excimer laser light is 193 nanometers, and the wave-length of $F_2$ eximer laser light is 157 nanometers. However, it is said that far ultraviolet rays and vacuum ultraviolet rays will be required for the 0.15 micron patterns. Researchers are now developing the photo-lithography using the ArF excimer laser light, and reports are published by Donald C. Hofer in Jouinal of Photopolymer Science and Technology, vol. 9, No. 3, pages 387 to 397, 1996.

However, as well as the high resolution, a highly sensitive photo-resist is required for the photo-lithography using the ArF excimer laser light or $F_2$ excimer laser light. This is because of the fact that the gas used for generating the laser light is short in lifetime. Moreover, the laser light is much liable to damage the lenses incorporated in the optical system.

In order to enhance the sensitivity of the photo-resist, a chemically amplified photo-resist is popular to the skilled persons. The chemically amplified photo-resist contains photoacid generator. The photoacid generator is a kind of photo-sensitive material, and accelerates the formation of latent images. A typical example of the chemically amplified photo-resist is disclosed in Japanese Patent Application laid-open No. 2-27660. The prior art chemically amplified photo-resist is composed of poly(p-tert-butoxycarbonyloxy-$\alpha$-methylstyrene) and photoacid generator. The photoacid generator is triphenylsulfonium hexafluoroarsenate. Hiroshi Ito and C. Grant Wilson report that the prior art chemically amplified photo-resist is widely used in the photo-lithography using the KrF excimer laser light (see American Chemical Society Symposium Series, vol. 242, pages 11–23, 1984).

When the chemically amplified photo-resist is exposed to the light, photoacid generator generates proton acid. After the pattern transfer through the exposure, the chemically amplified photo-resist is baked. Then, the proton acid gives rise to an acid-catalyzed reaction with the resist resin. By virtue of the acid-catalyzed reaction, the chemically amplified photo-resist achieves an extremely high sensitivity. The photo-reaction efficiency is defined as the amount of reaction per single photon. The standard photo-resist merely achieves the photo-reaction efficiency less than 1. However, the chemically amplified photo-resist achieves the photo-reaction efficiency drastically increased rather than the standard photo-resist. Most of the photo-resist presently developed are categorized in the chemically amplified photo-resist.

An example of the photoacid generator was developed by J. V. Crivello (see Journal of the Organic Chemistry, vol. 43, No. 15, pages 3055 to 3058, 1978). The photoacid generator is composed of the derivative of triphenylsulfonium salt, and is widely used for the chemically amplified photo-resist presently available.

The derivative of triphenylsulfonium salt is available for the chemically amplified photo-resist for the ArF excimer laser light lithography as reported by Nozaki et. al. in Journal of Photopolymer Science and Technology, vol. 10, No. 4, pages 545 to 550, 1997 and by Yamachika et. al. in Journal of Photopolymer Science and Technology, vol. 12, No. 4, pages 553 to 560, 1990. However, the derivative of triphenylsulfonium salt strongly absorbs the rays equal in wavelength to or less than 220 nanometers. When the chemically amplified photo-resist containing the derivative of triphenylsulfonium salt is used in the photo-lithography using the ray equal in wavelength to or less than 220 nanometers as the exposure light, the derivative of triphenylsulfonium salt is causative of reduction in transparency of the chemically amplified photo-resist, and, accordingly, the resolution is lowered as reported by Takuya Naitoh et. al. in the proceedings of the $8^{th}$ Lectures on Photo-Reactive Materials for Electric Devices, pages 16–18, 1999.

The photo-lithography using ArF excimer laser light is appropriate to the pattern transfer for extremely miniature patterns. For this reason, when the latent images are developed, the photo-resist mask has extremely narrow spaces, and the side surfaces defining the extremely narrow spaces are strongly influential in the uniformity of pattern. If the pattern edge roughness is poor, the ratio of the unevenness to the pattern width is large, and, accordingly, the uniformity of pattern becomes poor. Since the derivative of triphenylsulfonium salt absorbs the exposure light, the amount of exposure light is gradually reduced from the incident surface toward the back surface of the chemically amplified resist, and the contrast between the exposed portion and the non-exposed portion is made poor. This results in a low resolution and, accordingly, poor uniformity of the pattern. This is the problem inherent in the prior art chemically amplified photo-resist for the photo-lithography using the ultraviolet rays equal in wavelength to or less than 220 nanometers.

SUMMARY OF THE INVENTION

It is therefore an important object of the present invention to provide a photoacid generator, which keeps the transparency of resist resin high enough to achieve good pattern uniformity.

It is also an important object of the present invention to provide a chemically amplified photo-resist, which is transparent to 130–220 nanometer wavelength ultraviolet rays, high in photo-reaction efficiency, i.e., photoacid generating efficiency, high in resolution and low in pattern edge roughness.

It is another important object of the present invention to provide a pattern transfer method which is available for the ultra large scale integration in the next generation.

In accordance with one aspect of the present invention, there is provided a photoacid generator containing at least one first sulfonium salt compound selected from the group consisting of first sulfonium salt compounds expressed by general formula [1]

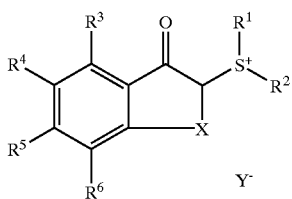

(1)

where each of $R^1$ and $R^2$ is straight chain, branching, monocyclic or cross-linked cyclic alkyl group, each of $R^3$, $R^4$, $R^5$ and $R^6$ is hydrogen atom, halogen atom, alkyl group having carbon number from 1 to 4 or alkoxyl group, X is —$CH_2$—, —$C_2H_2$— or —$OCH_2$— and $Y^-$ is a counter ion, and at least one second sulfonium salt compound selected from the group consisting of second sulfonium salt compounds expressed by general formula [2]

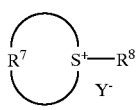

(2)

where $R^7$ is alkylene group or 2-oxoalkylene group, $R^8$ is straight chain, branching, monocyclic, polycyclic or cross-linked cyclic alkyl group having oxo group or straight chain, branching, monocyclic, polycyclic or cross-linked cyclic alkyl group without oxo group and $Y^-$ is a counter ion, and at least one of $R^7$ and $R^8$ has the oxo group.

In accordance with another aspect of the present invention, there is provided a chemically amplified photo-resist comprising a resin having at least one acid decomposable group and changing solubility in alkaline solution through an acid decomposition of the at least one acid decomposable group, and a photoacid generator containing at least one first sulfonium salt compound selected from the group consisting of first sulfonium salt compounds expressed by general formula [1]

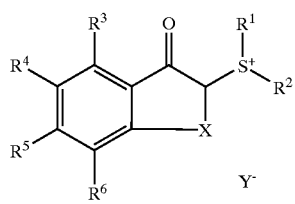

(1)

where each of $R^1$ and $R^2$ is straight chain, branching, monocyclic or cross-linked cyclic alkyl group, each of $R^3$, $R^4$, $R^5$ and $R^6$ is hydrogen atom, halogen atom, alkyl group having carbon number from 1 to 4 or alkoxyl group, X is —$CH_2$—, —$C_2H_4$— or —$OCH_2$— and $Y^-$ is a counter ion and at least one second sulfonium salt compound selected from the group consisting of second sulfonium salt compounds expressed by general formula [2]

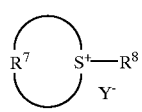

(2)

where $R^7$ is alkylene group or 2-oxoalkylene group, $R^8$ is straight chain, branching, monocyclic, polycyclic or cross-linked cyclic alkyl group having oxo group or straight chain, branching, monocyclic, polycyclic or cross-linked cyclic alkyl group without oxo group and $Y^-$ is a counter ion, at least one of $R^7$ and $R^8$ having the oxo group.

In accordance with yet another aspect of the present invention, there is provided a pattern transfer method comprising the steps of a) forming a chemically amplified photo-resist layer on a target layer, the chemically amplified photo-resist comprising a resin having at least one acid decomposable group and increasing solubility in alkaline solution through an acid decomposition of the at least one acid decomposable group, and a photoacid generator containing at least one first sulfonium salt compound selected from the group consisting of first sulfonium salt compounds expressed by general formula [1]

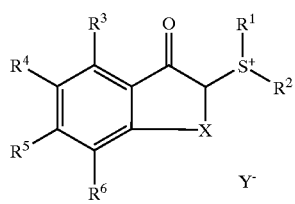

(1)

where each of $R^1$ and $R^2$ is straight chain, branching, monocyclic or cross-linked cyclic alkyl group, each of $R^3$, $R^4$, $R^5$ and $R^6$ is hydrogen atom, halogen atom, alkyl group having carbon number from 1 to 4 or alkoxyl group, X is —$CH_2$—, —$C_2H_4$— or —$OCH_2$— and $Y^-$ is a counter ion and at least one second sulfonium salt compound selected from the group consisting of second sulfonium salt compounds expressed by general formula [2]

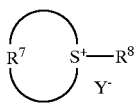

(2)

where $R^7$ is alkylene group or 2-oxoalkylene group, $R^8$ is straight chain, branching, monocyclic, polycyclic or cross-linked cyclic alkyl group having oxo group or straight chain, branching, monocyclic, polycyclic or cross-linked cyclic alkyl group without oxo group and $Y^-$ is a counter ion, at least one of $R^7$ and $R^8$ having the oxo group, b) exposing the chemically amplified photo-resist layer to light having a wavelength fallen within the range from 130 nanometers to 220 nanometers for producing a latent image therein, c) baking the chemically amplified photo-resist layer formed with the latent image, and d) developing the latent image.

BRIEF DESCRIPTION OF THE DRAWINGS

The features and advantages of the photoacid generator, the chemically amplified photo-resist and the pattern transfer method will be more clearly understood from the following description taken in conjunction with the accompanying drawings, in which.

DESCRIPTION OF THE PREFERRED EMBODIMENTS

Figure 1:
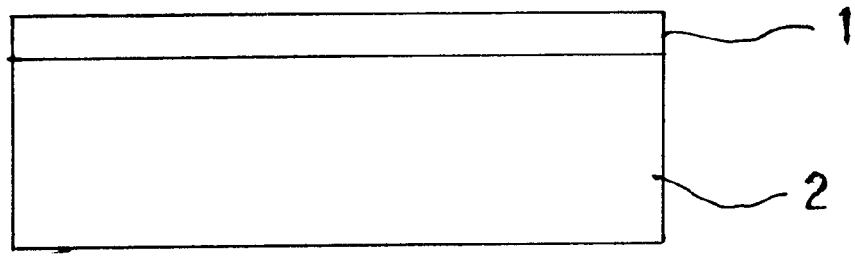
FIGS. 1A to 1E are schematic views showing a method for transferring a pattern according to the present invention.
Figure 1:
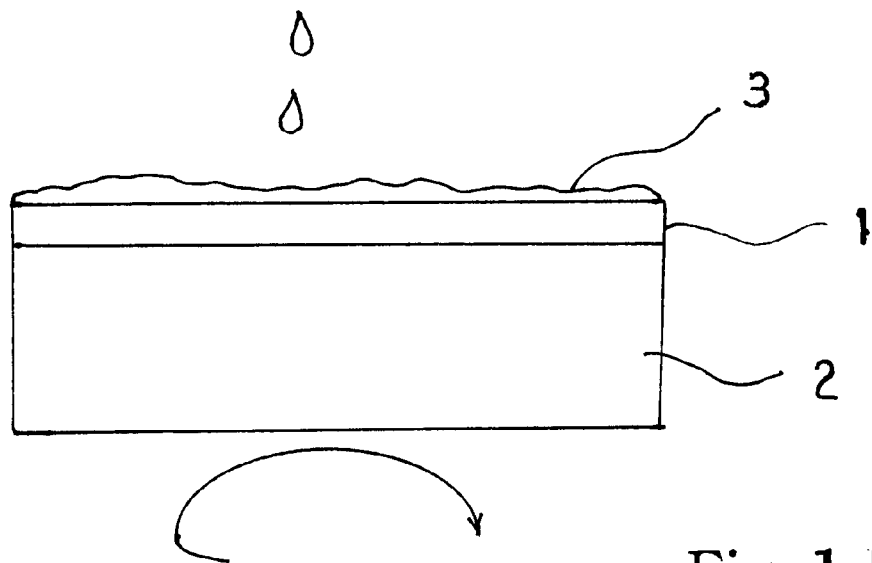
Figure 1:
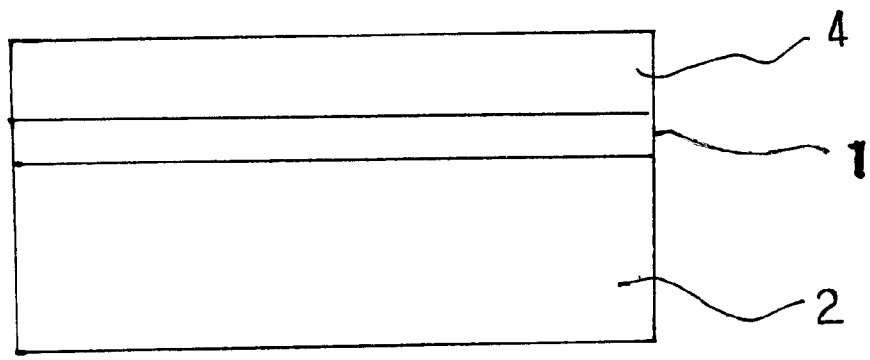
Figure 1:
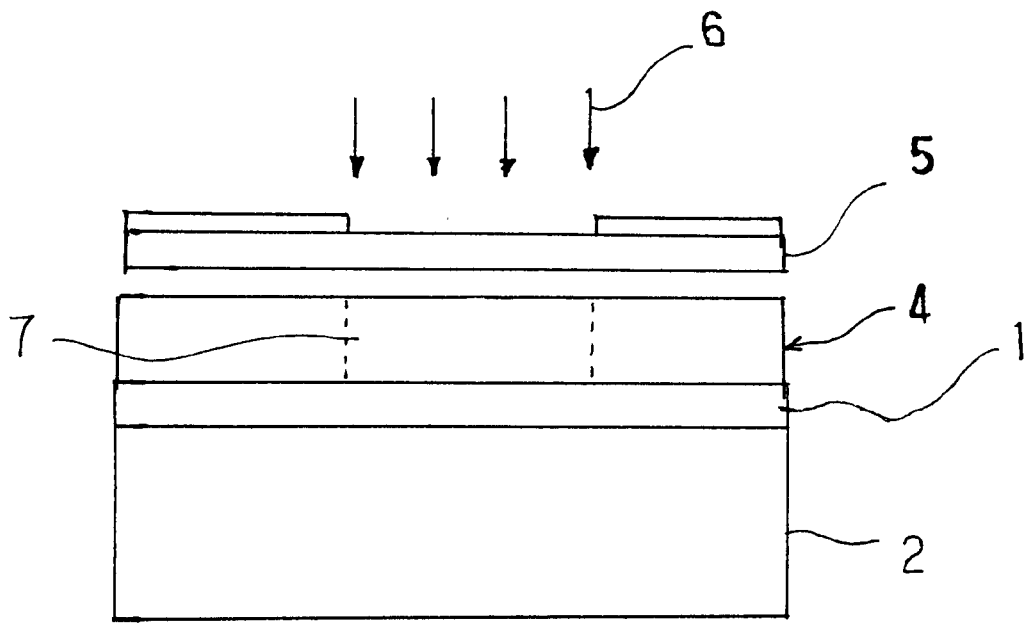
Figure 1:
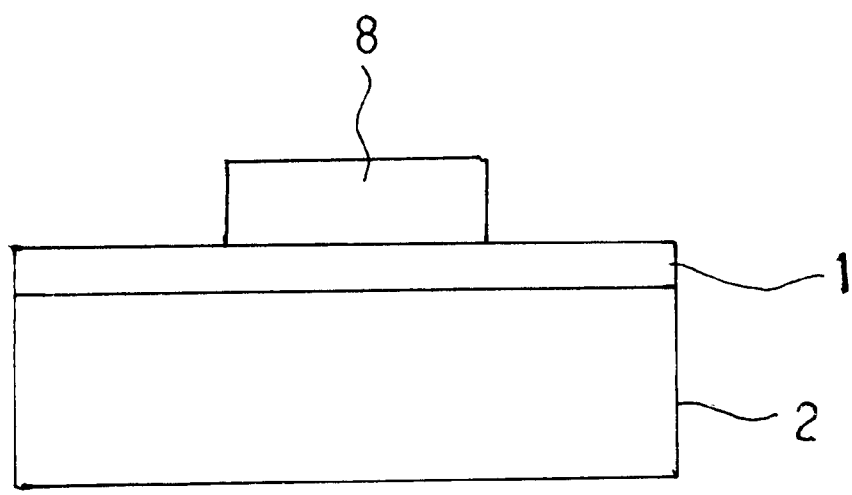

Description is hereinbelow made on photoacid generators embodying the present invention, compositions of chemically amplified photo-resist also embodying the present invention and a method for transferring a pattern embodying the present invention. Although the photoacid generators, the compositions of chemically amplified photo-resist and the method are preferable, they never set a limit to the technical scope of the present invention.

Photoacid Generator

Photoacid generator embodying the present invention contains two kinds of sulfonium salt compound expressed by general formulae [1] and [2]. It is preferable that the blending ratio between the sulfonium salt expressed by general formula [1] and the sulfonium salt expressed by general formula [2] is from 1:9 to 9:1.

In the following description, the sulfonium salt compound expressed by general formula [1] and the sulfonium salt compound expressed by general formula [2] are hereinbelow referred to as "first kind of sulfonium salt compound" and "second kind of sulfonium salt compound", respectively.

First Kind of Sulfonium Salt

In the general formula [1], each of $R^1$ and $R^2$ is alkyl group, and the alkyl group has the straight chain, branching, monocyclic or cross-linking cyclic structure.

Examples of the straight chain alkyl group are methyl group, ethyl group, n-propyl group, n-butyl group, n-pentyl group, n-hexyl group and n-heptyl group.

Examples of the branching alkyl group are iso-propyl group, iso-butyl group and tert-butyl group.

Examples of the monocyclic alkyl group are cyclopenthyl group, cyclohexyl group, cycloheptyl group and cyclooctyl group.

Examples of the cross-linking cyclic alkyl group are norbornyl group, isobornyl group, adamantyl group, tricyclodecyl group and tetracyclododecyl group.

$R^1$ and $R^2$ may be bonded to each other so as to form a ring. In this instance, the ring may be dihydric group with the above-described carbon skeleton, i.e., $—R^1—R^2—$ such as alkylene group and oxo-substituted alkylene group. Examples of the alkylene group are tetramethylene group and pentamethylene group, and examples of the oxo-substituted alkylene group are 2-oxotetramethylene group and 3-oxopentamethylene group.

Each of $R^3$, $R^4$, $R^5$ and $R^6$ in 1-oxoindane-2-yl group, 1-tetralone-2-yl group or 4-chromanone-2-yl group in general formula [1] is hydrogen atom, halogen atom such as, for example, fluorine atom, chlorine atom, bromine atom and iodine atom, alkyl group having carbon number from 1 to 4 such as, for example, methyl group, ethyl group, n-propyl group, isopropyl group, n-butyl group, isobutyl group and tert-butyl group or alkoxyl group such as, for example, methoxy group, ethoxy group and butoxy group.

Second Kind of Sulfonium Salt

In general formula [2], $R^7$ expresses alkylene group without oxo group or alkylene group having oxo group. The alkylene group may have either straight chain, branching, monocyclic, polycyclic or cross-linked cyclic structure. Examples of $R^7$ are propylene group, butylene group, pentylene group, hexylene group, heptylene group, oxopropylene group, oxobutylene group, oxopentylene group, oxohexylene group and oxoheptylene group.

In general formula [2], $R^8$ expresses straight-chain, branching, monocyclic, polycyclic or cross-linking cyclic alkyl group having oxo group or straight-chain, branching, monocyclic, polycyclic or cross-linking cyclic alkyl group without oxo group.

Examples of the straight-chain alkyl group having oxo group, branching alkyl group having oxo group, monocyclic alkyl group having oxo group, polycyclic alkyl group having oxo group and cross-linking cyclic alkyl group having oxo group are 2-oxo-propyl group, 2-oxo-butyl group, 2-oxo-3-methyl-butyl group, 2-oxo-3,3-dimethyl-butyl group, 2-oxo-pentyl group, 2-oxo-2-methyl-pentyl group, 2-oxo-3,3-dimethyl-pentyl group, 2-oxo-4methyl-pentyl group, 2-oxo-4,4-dimethyl-pentyl group, 2-oxo-4-ethyl-pentyl group, 2-oxo-3,3-diethyl pentyl group, 2-oxo-4-methyl-4-ethyl-pentyl group, 2-oxo-hexyl group, 2-oxo-3-methyl-hexyl group, 2-oxo-3,3-dimethyl-hexyl group, 2-oxo-4,4-dimethyl-hexyl group, 2-oxo-5,5-dimethyl-hexyl group, 2-oxo-3-ethyl-hexyl group, 2-oxo-4-ethyl-hexyl group, 2-oxo-heptyl group, 2-oxo-3-methyl-heptyl group, 2-oxo-4-methyl-heptyl group, 2-oxo-5-methyl-heptyl group, 2-oxo-6-methyl-heptyl group, 2-oxo-6,6-dimethyl-heptyl group, 2-oxo-3-ethyl-heptyl group, 2-oxo-4-ethyl-heptyl group, 2-oxo-5-ethyl-heptyl group, 2-oxo-3-propyl-heptyl group, 2-oxo-4-propyl-heptyl group, 2-oxo-octyl group, 2-oxo-3-methyl-octyl group, 2-oxo-4-methyl-octyl group, 2-oxo-5-methyl-octyl group, 2-oxo-6-methyl-octyl group, 2-oxo-7-methyl-octyl group, 2-oxo-7,7-dimethyl-octyl group, 2-oxo-3-ethyl-octyl group, 2-oxo-4-ethyl-octyl group, 2-oxo-5-ethyl-octyl group, 2-oxo-cyclopentyl group, 2-oxo-cyclohexyl group, 2-oxo-cycloheptyl group, 2-oxo-cyclopropylmethyl group, 2-oxo-methylcyclohexyl group, 2-oxo-cyclohexylmethyl group, 2-oxo-norbornyl group, 2-oxo-tricyclodecyl group, in which 2-oxo-tricyclo[5,2,1,0$^{2,}$ $_6$] decyl group is attractive, 2-oxo-tetracyclododecyl group, in which 2-oxo-tetracyclo [4.4.0$^{2,5}$.1$^{7,10}$] dodecyl group is attractive, 2-oxo-bornyl group, 2-oxo-2-cyclohexyl-ethyl group and 2-oxo-2-cyclopentyl-ethyl group.

Examples of the straight-chain alkyl group, branching alkyl group, mono-cyclic alkyl group, polycyclic alkyl group and cross-linking cyclic alkyl group are propyl group, butyl group, 2-methyl-butyl group, 3-methyl-butyl group, 3,3-dimethyl-butyl group, pentyl group, 2-methyl-pentyl group, 3-methyl-pentyl group, 4-methyl-pentyl group, 4,4-dimethyl-pentyl group, 2-ethyl-pentyl group, 3-ethyl-pentyl group, hexyl group, 3-methyl-hexyl group, 4-methyl-hexyl group, 5-methyl-hexyl group, 5,5-dimethyl-hexyl group, 2-ethyl-hexyl group, 3-ethyl-hexyl group, 4-ethyl-hexyl group, heptyl group, 2-methyl-heptyl group, 3-methyl-heptyl group, 4-methyl-heptyl group, 5-methyl-heptyl group, 6-methyl-heptyl group, 6,6-dimethyl-heptyl group, 2-ethyl-heptyl group, 3-ethyl-heptyl group, 4-ethyl-heptyl group, 5-ethyl-heptyl group, 2-ethyl-heptyl group, 3-ethyl-heptyl group, 4-propyl-heptyl group, octyl group, 2-methyl-octyl group, 3-methyl-octyl group, 4-methyl-octyl group, 5-methyl-octyl group, 6-methyl-octyl group, 7-methyl-octyl group, 7,7-dimethyl-octyl group, 2-ethyl-octyl group, 3-ethyl-octyl group, 4-ethyl-octyl group, 5-ethyl-octyl group, cyclopentyl group, cyclohexyl group, cycloheptyl group, cyclopropylmethyl group, methylcyclohexyl group, cyclohexylmethyl group, norbornyl group, tricyclodecyl group, in which tricyclo$[5.2.1.0^{2,6}]$ decyl group is attractive, adamantyl group, bornyl group and tetracyclododecyl group, in which tetracyclo$[4.4.0^{2,5}.1^{7,10}]$ dodecyl group is attractive.

In general formula [2], it is required that one of the groups expressed by $R^7$ and $R^8$ has oxo group.

In general formulae [1] and [2], $Y^-$ is a counter ion, and is perfluoroalkylsulfonate ion expressed by general formulae [3], the alkylsulfonate ion expressed by general formula [4], camphorsulfonate ion, benzensulfonate ion, alkylbenzensulfonate ion, fluorine-substituted benzensulfonate ion, fluorine-substituted alkylbenzensulfonate ion, fluoride ion or halogenide ion.

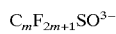  [3]

where m is a positive integer between 1 and 9.

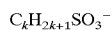  [4]

where k is an integer between 1 and 9.

Examples of the perfluoroalkylsulfonate ion is trifluoromethanesulfonate ion expressed as $CF_3SO_3^-$, nonafluorobutanesulfonate ion expressed as $C_4F_9SO_3^-$ and heptadecafluorooctanesulfonate ion expressed as $C_8F_{17}SO_3^-$.

Examples of the alkylsulfonate ion are methanesulfonate ion expressed as $CH_3SO_3^-$, ethanesulfonate ion expressed as $C_2H_5SO_3^-$, 1-octanesulfonate ion expressed as $C_8H_{17}SO_3^-$, 1-nonanesulfonate ion expressed as $C_9H_{19}SO^{3-}$.

Examples of the alkylbenzensulfonate ion are p-toluene sulfonate ion and xyleneslufonate ion.

Examples of the fluorine-substituted benzensulfonate ion are 4-fluorobenzensulfonate ion and pentafluorobenzensulfonate ion.

Examples of the fluorine-substituted alkylbenzensulfonate ion are 4-trifluoromethylbenzensulfonate ion and 3,5-bis(trifluoromethyl) benzensulfonate ion.

Examples of the fluoride ion are tetrafluoroborate ion expressed as $BF_4^-$, hexafluoroarsenate ion expressed as $AsF_6^-$, hexafluoroantimonate ion expressed as $SbF_6^-$ and hexafluorophosphate ion expressed as $PF_6^-$.

Examples of the halogenide ion are bromide ion expressed as $Br^-$ and iodide ion $I^-$.

Chemically Amplified Photo-Resist

The chemically amplified photo-resist according to the present invention contains the photoacid generator, resin and solvent. Positive chemically amplified photo-resist and negative chemically amplified photo-resist are produced in accordance with the present invention.

When the chemically amplified photo-resist except the residual solvent is expressed as being at 100 parts by weight, the chemically amplified photo-resist according to the present invention contains the photoacid generator at 0.2 part to 30 parts by weight and, more preferably, 1 part to 15 parts by weight. When the chemically amplified photo-resist merely contains the photoacid generator at 0.2 part or greater than 0.2 part by weight, the chemically amplified photo-resist is available for pattern transfer through the target light. If the chemically amplified photo-resist contains the photoacid generator at 1 part or greater than 1 part by weight, the chemically amplified photo-resist exhibits sufficient sensitivity to the target light, and a clear latent image is produced therein. On the other hand, when the photoacid generator exceeds 30 parts by weight, the chemically amplified photo-resist is hardly spread over a layer uniformly, and the scum is serious. If the photoacid generator is equal to or less than 15 parts by weight, the chemically amplified photo-resist layer is spread uniformly, and the scum is negligible.

The positive chemically amplified photo-resist according to the present invention is produced on the basis of the resist resin highly transparent to the exposure light, i.e., ultraviolet light with the wavelength equal to or less than 220 nanometers. The ultraviolet light fallen within the wavelength range is far ultraviolet rays and vacuum ultraviolet rays. The resin is further expected to become soluble in alkaline solution by virtue of the acid. When the chemically amplified photo-resist except the residual solvent is 100 parts, the resin is fallen within 60 parts to 99.8 parts and, more preferably, within 75 parts to 99 parts by weight.

The resin available for the positive chemically amplified photo-resist according to the present invention is, by way of example, the copolymer, which has (meth)acrylate unit containing 2,6-norbornanecarbolactone group (see Japanese Patent Application laid-open No. 2000-26446), the copolymer, which has alicyclic(meth)acrylate unit containing acid decomposition group (see Japanese Patent No. 2856116), the copolymer, which has 2-alkyladamantyl (meth)acrylate structural unit (see Journal of Photopolymer Science and Technology, vol. 10, No. 4, pages 545 to 550, 1997 and Japanese Patent Application laid-open No. 9-73173, the resin, which contains norbornene-maleic anhydride alternative copolymer unit (see Journal of Photopolymer Science and Technology, vol. 10, No. 3, pages 511 to 520, 1997 and Journal of Photopolymer Science and Technology, vol. 11, No. 3, pages 481 to 488, 1998), the resin, which has derivative of tetracyclododecene-maleic anhydride alternant copolymer unit (see Journal of Photopolymer Science and Technology, vol. 12, No. 4, pages 553–559, 1999), the derivative of polynorbornene (see Journal of Photopolymer Science and Technology, vol. 11, No. 3, pages 475–480, 1998 and Japanese Patent Application laid-open No. 10-218941), the resin, which is obtained through a ring-opening metathesis co-polymerization on derivative of norbornene and tetracyclododecene (see Japanese Patent Application laid-open No. 10-111569), the resin, which has norbornene-maleic anhydride alternative copolymer and 2-alkyladamantyl (meth)acrylate structural unit (see Japanese Patent Application laid-open No. 11-305444) or the copolymer, which has (meth)acrylate unit with lactone structure (see Japanese Patent Application laid-open No. 11-295894). These are examples of the resin used in the positive chemically amplified photo-resist. Any kind of resin is available for the positive chemically amplified photoresist according to the present invention in so far as the resin has the high transparency and the reactivity to the acid catalyst.

Resin available for the negative chemically amplified photo-resist is also expected to be highly transparent to the exposure light, i.e., the far ultraviolet rays and the vacuum ultraviolet rays having the wavelength equal to or less than 220 nanometers and insoluble in alkaline developer by virtue of the acid. When the negative chemically amplified photo-resist except the residual solvent is expressed to be 100 parts by weight, the resin is fallen within the range from 60 parts by weight to 99.8 parts by weight and, more preferably, from 70 parts by weight to 99 parts by weight.

An example of the resin available for the negative chemically amplified photo-resist according to the present invention is the resin disclosed in Journal of Photopolymer Science and Technology, vol. 12, No. 3, pages 487 to 492, 1999. Any kind of resin is available for the negative chemically amplified photo-resist in so far as the resin exhibits high transparency to the exposure light and reactivity to the acid catalyst.

When the ultraviolet rays are fallen onto a part of the negative chemically amplified photo-resist, the part becomes insoluble in the developer. In order to promote the production of the insoluble part, it is preferable to add cross linking agent to the negative chemically amplified photo-resist. The cross linking agents are, by way of example, in urea-melamine series and polyhydric alcohol. Examples of the cross linking agent in the urea-melamine series are hexamethoxymethylmelamine, 1,3,4,6-tetrakis (methoxymethyl) glycoluril, 1,3-bis (methoxymethyl)-4,5-bis (methoxymethyl) ethyleneurea and 1,3-bis (methoxymethyl) urea. Examples of the polyhydric alcohol are 2,3-dihydroxy-5-hydroxymethylnorbornane, 1,4-cyclohexandimethanol and 3,4,8(9)-trihydroxytricyclodecane. The above-described compounds do not set any limit to the cross linking agent available for the negative chemically amplified photo-resist according to the present invention. The negative chemically amplified photo-resist may contain only one cross linking agent. Otherwise, the negative chemically amplified photo-resist according to the present invention may contain more than one cross linking agent.

The chemically amplified photo-resist according to the present invention further contains solvent. Any organic solvent is available for the chemically amplified photo-resist in so far as the sulfonium salt compound and the resin are uniformly dissolved therein and the resultant chemically amplified photo-resist is uniformly spread over a target layer. Only one kind of organic solvent may be used. Of course, more than one kind of organic solvent may be blended.

Though not limited, examples of the solvent are n-propylalcohol, isopropylalcohol, n-butylalcohol, tert-butylalcohol, methyl cellosolve acetate, ethyl cellosolve acetate, propylene glycol ethyl ether acetate, methyl lactate, ethyl lactate, 2-methoxybutyl acetate, 2-ethoxyethyl acetate, methyl pyruvate, ethyl pyruvate, 3-methoxymethyl propionate, 3-methoxymethyl propionate, N-methyl-2-pyrrolidone, cyclohexanone, cyclopentanone, cyclohexanol, methylethylketone, 1,4-dioxan, ethylene glycol monomethyl ether, ethylene glycol monomethyl ether acetate, ethylene glycol monoethyl ether, ethylene glycol monoisopropyl ether, diethylene glycol monomethyl ether and diethylene glycol dimethyl ether.

The positive chemically amplified photo-resist and the negative chemically amplified photo-resist may further contain dissolution inhibitor, cross linking agent, basic compound, surface active agent, dye, stabilizer, spreading property improving agent and dyestuff, if necessary.

Pattern Transfer Method

The method starts with preparation of a layer to be overlaid by a photo-resist mask. In this instance, the layer is a semiconductor layer 1 grown on a silicon substrate 2 as shown in FIG. 1A. The chemically amplified photo-resist 3 is uniformly spread over the semiconductor layer 1 by using a spin coating as shown in FIG. 1B. The chemically amplified photo-resist 3 is either positive or negative. The chemically amplified photo-resist is formed into a chemically amplified photo-resist layer 4 through a soft baking as shown in FIG. 1C.

The resultant semiconductor substrate is put in an aligner, and a photo-mask 5 is moved over the chemically amplified photo-resist layer 4. The chemically amplified photo-resist layer 4 is exposed to light 6 through the photo-mask 5. The light 6 is, by way of example, ArF excimer laser light or $F_2$ excimer laser light, the wavelength of which is fallen within the range from 130 nanometers to 220 nanometers. A pattern image on the photo-mask 5 is transferred to the chemically amplified photo-resist layer 4, and a latent image 7 is produced in the chemically amplified photo-resist layer 4 as shown in FIG. 1D.

The chemically amplified photo-resist layer 4 is solidified through a hard baking, and the latent image is developed in appropriate developer. A photo-resist mask 8 is formed from the chemically amplified photo-resist layer 4 as shown in FIG. 1E. Using the photo-resist mask 8, the semiconductor layer 1 is etched, or is doped with dopant impurity through an ion-implantation.

Synthesis of Sulfonium Salt

Description is hereinbelow made on photoacid generator and chemically amplified photo-resist embodying the present invention. The present inventor firstly synthesized the two kinds of sulfonium salt compound for the photo-acid generator.

Synthesis 1

The present inventors synthesized an example of the first kind of sulfonium salt compound expressed by structural formula [5]

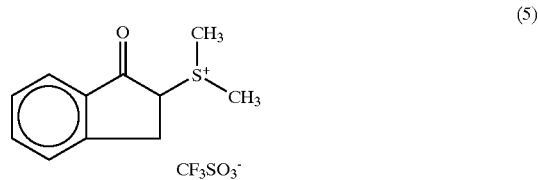

(5)

The structural formula [5] is equivalent to general formula [1] where X is methylene group, i.e., —$CH_2$—, $R^1$ and $R^2$ are methyl group, $R^3$, $R^4$, $R^5$ and $R^6$ are hydrogen atoms and $Y^-$ is trifluoromethanesulfonate ion.

The example of the first kind of sulfonium salt compound was synthesized through the following process. 10 grams of 2-bromo-1-indanone was dissolved in 50 milli-litter of ethanol. Water solution of methylmercaptane sodium salt at 15 percent was dropped by 25 milli-litter, and was agitated at room temperature for 3 hours. The mixture was poured into 300 milli-litter of cool water. Organic compound was extracted therefrom by using 200 milli-litter of ether.

The ether layer thus extracted was washed in water solution of sodium chloride and, thereafter, water. The ether layer was dried by using magnesium sulfate, and the ether was evaporated from the layer in low pressure. The residue was put in a silica gel column. Using eluate containing hexane and ethyl acetate at 7:1, the residue was separated and refined. Then, 3.2 grams of 2-(methylthio)-1-indanone remained. The yield was 38%.

Subsequently, 2 grams of 2-(methylthio)-1-indanone was dissolved in 10 milli-litter of nitromethane. 14 grams of methyl iodide was added thereto, and was agitated at room temperature. After an hour, 2.88 grams of silver trifluoromethanesulfonate was dissolved in 60 milli-litter of nitromethane, and the resultant mixture was dropped into the solution. Agitation was continued for 16 hours at room temperature. Then, silver iodide was precipitated, and the precipitate was filtrated. The filtrate was concentrated to a third in low pressure, and the concentrated filtrate was dropped into 200 mill i-litter of ether so that sulfonium salt was precipitated. The sulfonium salt was dissolved in acetone, and was precipitated in ether, again. The sulfonium salt expressed by structural formula [5] was crystallized from ethyl acetate-ethanol. The sulfonium salt was 2.95 grams. The yield was 80%, and the melting point was 132 degrees in centigrade. An NMR analysis data were $^1$H-NMR (THF-$d_8$); 3.14 (3H, s), 3.20 (3H, s), 3.74–3.95 (2H, m), 4.87–5.02 (1H, m), 7.38–7.85 (4H, m).

Synthesis 2

The present inventor further synthesized another example of the first kind of sulfonium salt compound expressed by structural formula [6].

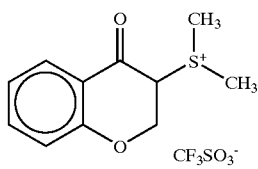

(6)

The structural formula [6] is equivalent to general formula [1] where X is —OCH$_2$—, R$^1$ and R$^2$ are methyl group, R$^3$, R$^4$, R$^5$ and R$^6$ are hydrogen atoms and Y$^-$ is trifluoromethanesulfonate ion.

The sulfonium salt compound expressed by structural formula [6] was synthesized as follows. First, the present inventor prepared 3-bromo-4-chromanone. The 3-bromo-4-chromanone was synthesized in accordance with the report by W. S. Johnson et. al. in J. Am. Chem. Soc., vol. 66, pages 218–220, 1944. 10.4 grams of 3-bromo-4-chromanone was dissolved in 42 milli-litters of ethanol. 21.3 milli-litters of 15% water solution of methyl-mercaptan sodium salt was dropped thereinto. The resultant solution was agitated at room temperature for 2 hours, and the resultant mixture was poured into cold water. An organic layer was extracted by using 200 milli-litters of ether, and the ether layer was washed in sodium chloride and, thereafter, water. The ether layer was dried by using magnesium sulfate, and the solvent was removed in low pressure. The residue was put in a silica gel column. Using eluate containing hexane and ethyl acetate at 3:1, the residue was separated and refined. Then, 1.52 grams of 3-methylthio-4-chromanone was obtained. The yield was 17%.

Subsequently, 1.48 grams of 3-methylthio-4-chromanone was dissolved in 8 milli-litter of nitromethane. 9.73 grams of methyl iodide was added thereto, and was agitated at room temperature. After an hour, 1.958 grams of silver trifluoromethanesulfonate was dissolved in 40 milli-litter of nitromethane, and the resultant mixture was dropped into the solution. Agitation was continued for 20 hours at room temperature. Then, silver iodide was precipitated, and the precipitate was filtrated. The filtrate was concentrated to a third in low pressure, and the concentrated filtrate was dropped into 200 milli-litter of ether so that sulfonium salt was precipitated. The sulfonium salt was dissolved in acetone, and was precipitated in ether, again. The sulfonium salt expressed by structural formula [6] was recrystallized from ethyl acetate-ethanol. The sulfonium salt was 1.77 grams. The yield was 65%, and the melting point was 113 degrees in centigrade.

Synthesis 3

The present inventor further synthesized yet another example of the first kind of sulfonium salt compound expressed by structural formula [7].

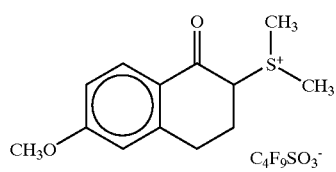

(7)

The structural formula [7] is equivalent to general formula [1] where X is ethylene group, i.e., —C$_2$H$_4$—, R$^1$ and R$^2$ are methyl group, R$^3$, R$^4$ and R$^6$ are hydrogen atoms, R$^5$ is methoxy group and Y$^-$ is nonafluorobutanesulfonate ion.

The sulfonium salt compound expressed by structural formula [7] was synthesized as follows.

First, 4.628 grams of 6-metoxy-2-(methylthio)-1-tetralone was dissolved in 30 milli-litter of acetonitrile. 6.54 grams of methyl nonafluorobutanesulfonate, which was dissolved in 10 milli-litter of acetonitrile, was dropped thereinto under icing. The resultant solution was placed in a cold storage all night. The resultant solution was poured into 250 milli-litter of ether. Then, salt was precipitated, and was filtrated. The salt was dissolved in acetonitrile, and precipitated in ether, again. The salt was filtrated, and was recrystallized in solvent of ethyl acetate-acetonitrile Then, 6.33 grams of sulfonium salt expressed by structural formula [7] was obtained. The yield was 57%, and the melting point was 143 degrees in centigrade. An NMR analysis result was H-NMR (acetone-$d_6$): 2.49–2.63 (1H, br), 3.12–3.17 (3H, m), 3.29 (6H, s), 3.93 (3H, s), 5.28 (1H, dd), 6.9–7.07 (2H, m), 7.96(1H, d).

Synthesis 4

The present inventors synthesized 2-oxobutyl-thiacyclohexanium bromide expressed by structural formula [8].

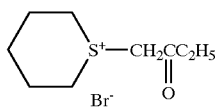

(8)

The synthesis was carried out under radiation from a yellow lamp. A 100-millilitter three-port flask was prepared. Using the flask, 4 grams of pentamethylenesulfide was dissolved in 40 milli-litter of acetone. 6 grams of 1-bromo-2-butanone was dropped into the solution over agitation. After 24 hours, white crystal was precipitated, and was filtrated. The white crystal was pulverized, and the pulverized white crystal was washed in ether. The resultant crystal was dried by using a low-pressure drier at 30 degrees in centigrade for six hours. Then, 7.2 grams of 2-oxobutyl-thiacyclohexanium bromide was obtained. The yield was 72.5%.

Using an NMR analyzer AMX400 manufactured by Bruker Instrument Inc., the synthetic compound was analyzed. The analysis was resulted as $^1$H-NMR(CDCl$_3$, internal standard substance was tetramethylsilane): δ (ppm) 1.11–1.18 (t, 3H—CH$_3$), 1.85–1.91 (m, 4H, —CH$_2$—), 2.27–2.39 (m, 2H, —CH$_2$—), 2.67–2.81(m, 2H, —CH$_2$—), 3.73–3.86 (m, 2H, S$^+$—CH$_2$—), 4.09–4.12 (m, 2H S$^+$—CH$_2$—), 5.77 (s, 2H, S$^+$—CH$_2$—C(O)—).

| Ultimate Analysis | C | H | S |
| --- | --- | --- | --- |
| Actual value (weight %) | 42.69 | 6.77 | 12.66 |
| Theoretical value (weight %) | 42.50 | 6.85 | 12.53 |

The theoretical value was calculated on the basis of C$_9$H$_{17}$BrOS, the molecular weight of which was 253.19.

Synthesis 5

The present inventors synthesized 2-oxobutyl-thiacyclohexnium trifluoromethanesulfonate expressed by structural formula [9]

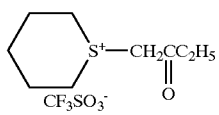

(9)

The synthesis was carried out under radiation from a yellow lamp. Using the 300-milliliter 3-port flask, 2 grams of 2-oxobutyl-thiacyclohexanium bromide, which was obtained through "Synthesis 4", was dissolved in 10 milli-liter of acetonitrile. 1.5 grams of potassium trifluoromethanesulfonate, which was dissolved in 100 milli-litter of acetonitrile, was dropped into the solution. Agitation was continued for 3 hours. Potassium bromide was precipitated, and was filtrated. The acetonitrile was evaporated in low-pressure by using an evaporator. The residue was dissolved in chloroform, and insoluble material was filtrated. The chloroform was evaporated from the filtrate in low-pressure, and transparent viscous liquid was cooled at −20 degrees in centigrade for 3 hours by using a refrigerator. The transparent viscous liquid was converted to white crystal through the refrigeration. The white crystal was recrystallized in ethyl acetate. The recrystallized white crystal was dried at 30 degrees in centigrade for 6 hours in low-pressure. 1.92 grams of 2-oxobutyl-thiacyclohexnium trifluoromethanesulfonate was obtained. The yield was 75.4%, the melting point was 51.4 degrees in centigrade, and the thermal decomposition point was 212.8 degrees in centigrade.

The synthesis compound was analyzed by using the NMR, and the analysis result was $^1$H-NMR(CDCl$_3$, internal standard substance was tetramethylsilane): δ (ppm) 1.04–1.11 (t, 3H—CH$_3$), 1.82–1.92 (m, 4H, —CH$_2$—), 2.14–2.26 (m, 2H, —CH$_2$—), 2.65–2.70(m, 2H, —CH$_2$—), 3.42–3.46 (m, 2H, S$^+$—CH$_2$—), 3.42–3.46 (m, 2H S$^+$—CH$_2$—), 3.56–3.59 (m, 2H S$^+$—CH$_2$—), 4.89 (S, 2H, S$^+$—CH$_2$—C(O)—).

| Ultimate Analysis | C | H | S |
| --- | --- | --- | --- |
| Actual value (weight %) | 47.26 | 5.32 | 19.89 |
| Theoretical value (weight %) | 47.26 | 5.40 | 19.99 |

The theoretical value was calculated on the basis of C$_{10}$H$_{17}$F$_3$O$_4$S$_2$, the molecular weight of which was 322.35.

Synthesis 6

The present inventors synthesized 2-oxobutyl-thiacyclohexanium heptadecafluorooctanesulfonate expressed by structural formula [10].

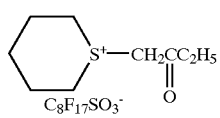

(10)

The synthesis was carried out under radiation from a yellow lamp. The synthesis was similar to the "Synthesis 5" except that 1.5 grams of potassium trifluoromethanesulfonate was replaced with 5.38 grams of potassium heptadecafluorooctanesulfonate. 1.54 grams of 2-oxobutyl-thiacyclohexanium heptadecafluorooctanesulfonate was obtained. The yield was 58%.

The synthesis compound was analyzed by using the NMR. The analysis result was $^1$H-NMR(CDCl$_3$, internal standard substance was tetramethylsilane): δ (ppm) 1.05–1.11 (t, 3H—CH$_3$), 1.82–1.92 (m, 4H, —CH$_2$—), 2.24–2.28 (m, 2H, —CH$_2$—), 2.66–2.71(m, 2H, —CH$_2$—), 3.48–3.46 (m, 2H, S$^+$—CH$_2$—), 3.42–3.62 (m, 2H S$^+$—CH$_2$—), 4.99 (S, 2H, S$^+$—CH$_2$—C(O)—).

| Ultimate Analysis | C | H | S |
| --- | --- | --- | --- |
| Actual value (weight %) | 30.37 | 2.55 | 9.54 |
| Theoretical value (weight %) | 30.65 | 2.41 | 9.88 |

The theoretical value was calculated on the basis of C$_{17}$H$_{17}$F$_{17}$O$_4$S$_2$, the molecular weight of which was 672.41.

Synthesis 7

The present inventors synthesized 2-oxo-3,3-dimethylbutyl-thiacyclopentanium bromide expressed by structural formula [11].

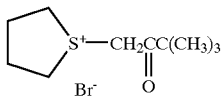

(11)

Using the 100-millilitter 3-port flask, 2 grams of tetrahydrothiophene was dissolved in 20 milli-litter of acetone. 4.87 grams of 1-bromo-3,3-dimethyl-2-butanone was dropped into the solution over agitation. After 24 hours, white crystal was precipitated, and was filtrated. The white crystal was pulverized, and was washed in ether. The pulverized white crystal was dried at 30 degrees in centigrade for 6 hours by using a low-pressure drier. 5.15 grams of 2-oxo-3,3-dimethylbutyl-thiacyclopentanium bromide was obtained. The yield was 75.0%.

The synthesis compound was analyzed by using the NMR. The analysis result was $^1$H-NMR(CDCl$_3$, internal standard substance was tetramethylsilane): δ (ppm) 1.28–1.33 (t, 9H—CH$_3$), 2.34–2.41 (m, 2H, —CH$_2$—), 2.56–2.63 (m, 2H, —CH$_2$—), 2.74–2.81(m, 2H, —CH$_2$—), 3.77–3.88 (m, 4H, S$^+$—CH$_2$—), 5.5 (S, 2H, S$^+$—CH$_2$—C(O)—).

| Ultimate Analysis | C | H | S |
|---|---|---|---|
| Actual value (weight %) | 45.08 | 7.10 | 11.95 |
| Theoretical value (weight %) | 44.95 | 7.17 | 12.00 |

The theoretical value was calculated on the basis of C$_{10}$H$_{19}$BrOS, the molecular weight of which was 267.22.

Synthesis 8

The present inventors synthesized 2-oxo-3,3-dimethylbutyl-thiacyclopentanium nonafluorobutanesulfonate expressed by structural formula [12].

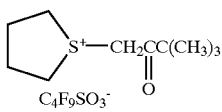

(12)

The synthesis was carried out under radiation from a yellow lamp. The synthesis was similar to the "Synthesis 5" except that the potassium trifluoromethanesulfonate and the 2-oxo-3,3-dimethylbutyl-thiacyclopentanium bromide were replaced with potassium nonafluorobutanesulfonate and 2-oxo-3,3,-dimethylbutyl-thiacyclopentanium bromide, respectively. The present inventors obtained 2-oxo-3,3-dimethylbutyl-thiacyclopentanium nonafluorobutanesulfonate. The yield was 52%, and the melting point was 79.5 degrees in centigrade.

The synthesis compound was analyzed by using the NMR. The analysis result was $^1$H-NMR(CDCl$_3$, internal standard substance was tetramethylsilane): δ (ppm) 1.23–1.27 (t, 9H—CH$_3$), 2.23–2.31 (m, 2H, —CH$_2$—), 2.45–2.50 (m, 2H, —CH$_2$—), 2.46–3.50(m, 2H, S$^+$—CH$_2$—), 3.63–3.70 (m, 2H, S$^+$—CH$_2$—), 4.97 (S, 2H, S+—CH$_2$—C(O)—).

| Ultimate Analysis | C | H | S |
|---|---|---|---|
| Actual value (weight %) | 34.45 | 3.80 | 13.99 |
| Theoretical value (weight %) | 34.57 | 3.94 | 13.18 |

The theoretical value was calculated on the basis of C$_{14}$H$_{19}$F$_9$O$_4$S$_2$, the molecular weight of which was 486.40.

Transparency to 193.4 nm Wavelength Light

The present inventors evaluated the transparency of the sulfonium salt compound obtained through the "Synthesis 1". The present inventors prepared an ultraviolet-visual light spectrophotometer UV-365 manufactured by Shimadzu Corporation. 3.1 milli-grams of the sulfonium salt compound was dissolved in 25 milli-litter of acetonitrile. Using a quartz cell having an optical path of 1 millimeter long, the absorption spectrum of the solution was measured by means of the ultra violet-visual light spectrophotometer. The present inventors determined the absorbance and the molar absorbance to 193.4 nanometer wavelength light, which was ArF excimer laser light. Similarly, the present inventors determined the molar absorbance of the sulfonium salt compounds obtained through the "Synthesis 2", "Synthesis 5"and "Synthesis 8". The present inventors further determined the molar absorbance of a prior art photoacid generator. The prior art photoacid generator was triphenylsulfonium trifluoromethanesulfonate TPS-105 manufactured by Midori Kagaku Co., Ltd.

The molar absorbance was tabled as follows.

TABLE 1

| | Molar absorbance to 193.4 nm light (1 · mol$^{-1}$ · cm$^{-1}$) |
|---|---|
| Sulfonium salt obtained through Synthesis 1 | 16052 |
| Sulfonium salt obtained through Synthesis 2 | 12082 |
| Sulfonium salt obtained through Synthesis 5 | 445 |
| Sulfonium salt obtained through Synthesis 8 | 644 |
| TPS: (C$_6$H$_5$)S$^+$CF$_3$SO$_3^-$ | 54230 |

From Table 1, it was understood that the sulfonium salt compounds according to the present invention were superior in transparency to ArF excimer laser light to the prior art triphenylsulfonium salt.

Pattern Transfer Characteristics

The present inventors prepared samples of positive chemically amplified photo-resist as follows. Resin used for the positive chemically amplified photo-resist was expressed by structural formula [13] where tBu stood for tert-butyl group.

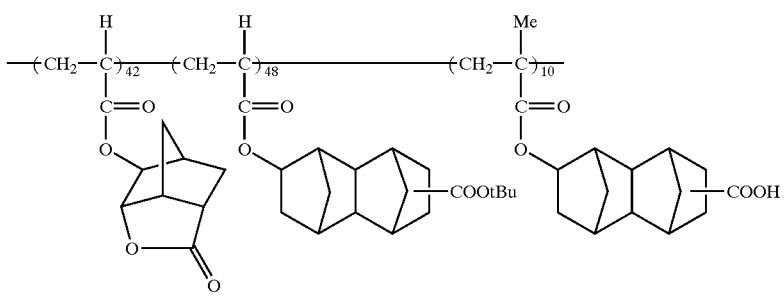

(13)

The photoacid generator contained in the samples was described in Table 2, and the solvent was propylene glycol monomethyl ether acetate. 2 grams of the resin, 0.04 gram of the photoacid generator (see Table 2) and 11.5 grams of propylene glycol monomethyl ether acetate were mixed, and the mixture was filtrated through a 0.2 micron Teflon filter. Thus, the present inventors obtained samples of the positive chemically amplified photo-resist. The present inventors further produced comparative samples, which contained only one of the two kinds of sulfonium salt compounds or the prior art photoacid generator TPS-105. In Table 2, samples 1 to 4 were fallen within the technical scope of the present invention, and samples 5, 6 and 7 were produced for the comparative use.

The present inventors prepared 8-inch silicon wafers, and the 8-inch silicon wafers were coated with organic anti-reflection layers of 0.1 micron thick. The organic anti-reflection layers were formed from DUV-30J manufactured by Brewer Corporation. The samples and the comparative samples were spun onto the organic anti-reflection layers, respectively, and were baked on a hot plate at 110 degrees in centigrade for a minute. The samples and the comparative samples were formed into positive chemically amplified photo-resist layers of 0.4 micron thick.

An ArF reduction projection aligner manufactured by Nikon Corporation was used for in the evaluation. The numerical aperture of the reduction projection aligner was 0.6. Using the ArF reduction projection aligner, the present inventors exposed the positive chemically amplified photo-resist layers to the ArF excimer laser light through a photomask. A line-and-space pattern was formed on the photomask, and a latent image was produced in the positive chemically amplified photo-resist layers.

After the exposure to the light, the positive chemically amplified photo-resist layers were immediately baked on the hot plate at 130 degrees in centigrade for 60 seconds. Subsequently, the present inventors dipped the positive chemically amplified photo-resist layers into water solution of 2.38% TMAH [$(CH_3)_4NOH$] at 23 degrees in centigrade for 60 seconds so as to develop the latent image. After the development, the positive chemically amplified photo-resist layers were rinsed in pure water for 60 seconds. The exposed portions of the positive chemically amplified photo-resist layers were removed from the silicon wafers, and a positive line-and-space pattern was formed on each of the silicon wafers.

The present inventors observed the side surfaces of the line-and-space pattern on each silicon wafer through a scanning electron microscope, and evaluated the smoothness of the side surfaces. When the side surfaces of a certain sample were smoother than the side surfaces of sample 7, the present inventors marked the sample with ○. If the side surfaces of another sample were as rough as those of sample 7, the present inventors marked the sample with △. The present inventors further evaluated the resolution and the sensitivity. The smoothness, the resolution and the sensitivity were written in Table 2. In Table 2, "Synthesis n" means the sulfonium salt compound obtained through the above-described "Synthesis n".

TABLE 2

| Sample | Photoacid Generator (blending ratio by weight) | Resolution ($\mu$mL/S) | Sensitivity (mJ/cm$^2$) | Smoothness of Side Surface |
|---|---|---|---|---|
| 1 | Synthesis 1 and Synthesis 5 (1:2) | 0.14 | 24 | ○ |
| 2 | Synthesis 1 and Synthesis 8 (1:4) | 0.14 | 36 | ○ |
| 3 | Synthesis 3 and Synthesis 5 (1:2) | 0.14 | 26 | ○ |
| 4 | Synthesis 3 and Synthesis 8 (1:3) | 0.14 | 30 | ○ |
| 5 | Synthesis 3 | 0.15 | 18 | △ |
| 6 | Synthesis 8 | 0.15 | 80 | △ |
| 7 | TPS-105 | 0.15 | 16 | |

From Table 2, it was understood that the chemically amplified photo-resist containing both first and second kinds of sulfonium salt compounds achieved high resolution and good smoothness.

The present inventors prepared samples of negative chemically amplified photo-resist. Resin used for the negative chemically amplified photo-resist was expressed by structural formula [14].

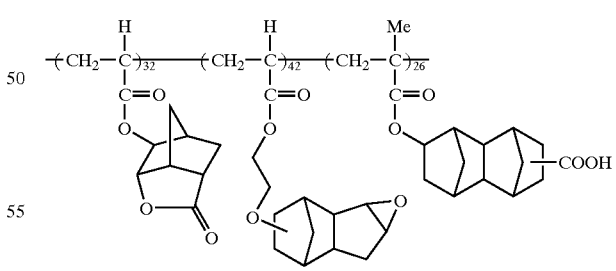

(14)

The photoacid generator contained in the samples was described in Table 3. The cross linking agent was 2,3-dihydroxy-5-hydroxymethylnorbornane, and solvent was ethyl lactate. The present inventor mixed 2 grams of the resin, 0.04 gram of the photoacid generator and 0.3 gram of the cross linking agent in the solvent. The mixture was filtrated through a 0.2 micron Teflon filter so as to prepare samples of the negative chemically amplified photo-resist. Comparative samples were similarly prepared (see Table 3).

The samples were spun onto 8-inch silicon wafers, and were baked on a hot plate at 80 degrees in centigrade for a minute. Then, the 8-inch silicon wafers were covered with negative chemically amplified photo-resist layers of 0.4 micron thick, respectively. Using the above-described ArF reduction projection aligner, the present inventors exposed the negative chemically amplified photo-resist layers to the ArF excimer laser light through a photo-mask. A line-and-space pattern was formed on the photo-mask, and a latent image was produced in the negative chemically amplified photo-resist layers.

After the exposure to the light, the negative chemically amplified photo-resist layers were immediately baked on the hot plate at 130 degrees in centigrade for 60 seconds. Subsequently, the present inventors dipped the negative chemically amplified photo-resist layers into water solution of 2.38% TMAH [$(CH_3)_4NOH$] at 23 degrees in centigrade for 60 seconds for developing the latent image. After the development, the negative chemically amplified photo-resist layers were rinsed in pure water for 60 seconds. The non-exposed portions of the chemically amplified photo-resist layers were removed from the silicon wafers, and a negative line-and-space pattern was formed on each of the silicon wafers.

The present inventors observed the side surfaces of the line-and-space pattern on each silicon wafer through the scanning electron microscope, and evaluated the smoothness of the side surfaces. When the side surfaces of a certain sample were smoother than the side surfaces of sample 5, the present inventors marked the sample with "○". If the side surfaces of another sample were as rough as those of sample 5, the present inventors marked the sample with "Δ". The present inventors further evaluated the resolution and the sensitivity. The smoothness, the resolution and the sensitivity were written in Table 3.

TABLE 3

| Sample | Photoacid Generator (blending ratio by weight) | Resolution ($\mu$mL/S) | Sensitivity (mJ/cm$^2$) | Smoothness of Side Surfaces |
|---|---|---|---|---|
| 1 | Synthesis 1 and Synthesis 5 (1:2) | 0.13 | 12 | ○ |
| 2 | Synthesis 3 and Synthesis 8 (1:3) | 0.13 | 16 | ○ |
| 3 | Synthesis 3 | 0.15 | 10 | Δ |
| 4 | Synthesis 8 | 0.15 | 48 | Δ |
| 5 | TPS-105 | 0.13 | 7 | Δ |

From Table 3, it was understood that the chemically amplified photo-resist containing both first and second kinds of sulfonium salt compounds achieved high resolution and good smoothness.

As will be appreciated from the foregoing description, the photoacid generator according to the present invention keeps the resin highly transparent to the 130–220 wavelength ultraviolet rays. The chemically amplified photo-resist according to the present invention creates smooth side surfaces of a pattern after development. Finally, a pattern transfer method according to the present invention is available for the ultra large scale integration in the next generation.

Although particular embodiments of the present invention have been shown and described, it will be apparent to those skilled in the art that various changes and modifications may be made without departing from the spirit and scope of the present invention.

What is claimed is:

1. A photoacid generator containing at least one first sulfonium salt compound selected from the group consisting of first sulfonium salt compounds expressed by general formula [1]

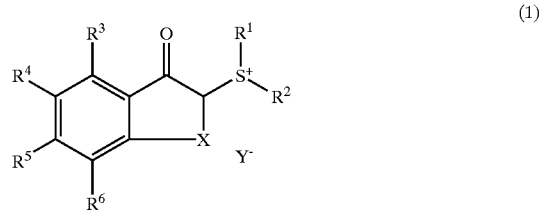

where each of $R^1$ and $R^2$ is straight chain, branching, monocyclic or cross-linked cyclic alkyl group, or $R^1$ and $R^2$ form a ring, each of $R^3$, $R^4$, $R^5$ and $R^6$ is hydrogen atom, halogen atom, alkyl group having carbon number from 1 to 4 or alkoxyl group, X is —$CH_2$—, —$C_2H_4$— or —$COCH_2$— and $Y^-$ is a counter ion, and at least one second sulfonium salt compound selected from the group consisting of second sulfonium salt compounds expressed by general formula [2]

where $R^7$ is alkylene group or 2-oxoalkylene group, $R^8$ is straight chain, branching, monocyclic, polycyclic or cross-linked cyclic alkyl group having oxo group or straight chain, branching, monocyclic, polycyclic or cross-linked cyclic alkyl group without oxo group and $Y^-$ is a counter ion, at least one of $R^7$ and $R^8$ having said oxo group.

2. The photoacid generator as set forth in claim 1, in which said $R^1$ and said $R^2$ form a group having a saturated carbon skelton.

3. The photoacid generator as set forth in claim 2, in which said group is oxo substituted alkylene group.

4. The photoacid generator as set forth in claim 1, in which said $Y^-$ is anion selected from the group consisting of perfluoroalkylsulfonate ions expressed by general formula [3], alkylsulfonate ions expressed by general formula [4], camphorsulfonate ions, benzensulfonate ions, alkylbenzensulfonate ions, fluorine-substituted benzensulfonate ions, fluorine-substituted alkylbenzensulfonate ions, fluoride ions and halogenide ions

where m is a positive integer between 1 and 9,

where k is a positive integer between 1 and 9.

5. The photoacid generator as set forth in claim 4, in which said fluoride ions are $BF_4^-$, $AsF_6^-$, $SbF_6^-$ and $PF_6^-$.

6. The photoacid generator as set forth in claim 4, in which said halogenide ions are $Br^-$ and $I^-$.

7. A chemically amplified photo-resist comprising:

a resin having at least one acid decomposable group and changing solubility in alkaline solution through an acid decomposition of said at least one acid decomposable group; and a photoacid generator containing at least one first sulfonium salt compound selected from the group consisting of first sulfonium salt compounds expressed by general formula [1]

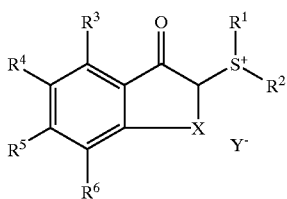

(1)

where each of $R^1$ and $R^2$ is straight chain, branching, monocyclic or cross-linked cyclic alkyl group, or $R^1$ and $R^2$ from a ring, each of $R^3$, $R^4$, $R^5$ and $R^6$ is hydrogen atom, halogen atom, alkyl group having carbon number from 1 to 4 or alkoxyl group, X is —$CH_2$—, —$C_2H_4$— or —$OCR_2$— and $Y^-$ is a counter ion, and at least one second sulfonium salt compound selected from the group consisting of second sulfonium salt compounds expressed by general formula [2]

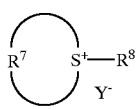

(2)

where $R^7$ is alkylene group or 2-oxoalkylene group, $R^8$ is straight chain, branching, monocyclic, polycyclic or cross-linked cyclic alkyl group having oxo group or straight chain, branching, monocyclic, polycyclic or cross-linked cyclic alkyl group without oxo group and $Y^-$ is a counter ion, at least one of $R^7$ and $R^8$ having said oxo group.

8. The chemically amplified photo-resist as set forth in claim 7, in which said $R^1$ and said $R^2$ form a group having a saturated carbon skeleton.

9. The chemically amplified photo-resist as set forth in claim 8, in which said group is oxo substituted alkylene group.

10. The chemically amplified photo-resist as set forth in claim 7, in which said $Y^-$ is anion selected from the group consisting of perfluoroalkylsulfonate ions expressed by general formulae [3], alkylsulfonate ions expressed by general formula [4], camphorsulfonate ions, benzensulfonate ions, alkylbenzensulfonate ions, fluorine-substituted benzensulfonate ions, fluorine-substituted alkylbenzensulfonate ions, fluoride ions and halogenide ions

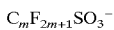

[3]

where m is a positive integer between 1 and 9,

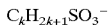

[4]

where k is a positive integer between 1 and 9.

11. The chemically amplified photo-resist as set forth in claim 7, further comprising a solvent.

12. The chemically amplified photo-resist as set forth in claim 11, further comprising a cross-linking agent.

13. A pattern transfer method comprising the steps of:
a) forming a chemically amplified photo-resist layer on a target layer, said chemically amplified photo-resist comprising a resin having at least one acid decomposable group and increasing solubility in alkaline solution through an acid decomposition of said at least one acid decomposable group, and a photoacid generator containing at least one first sulfonium salt compound selected from the group consisting of first sulfonium salt compounds expressed by general formula [1]

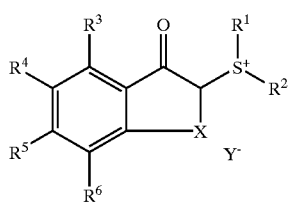

(1)

where each of $R^1$ and $R^2$ is straight chain, branching, monocyclic or cross-linked cyclic alkyl group, or $R^1$ and $R^2$ form a ring, each of $R^3$, $R^4$, $R^5$ and $R^6$ is hydrogen atom, halogen atom, alkyl group having carbon number from 1 to 4 or alkoxyl group, X is —$CH_2$—, —$C_2H_4$— or —$OCH_2$— and $Y^-$ is a counter ion, and at least one second sulfonium salt compound selected from the group consisting of second sulfonium salt compounds expressed by general formula [2]

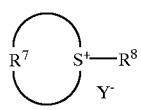

(2)

where $R^7$ is alkylene group or 2-oxoalkylene group, $R^8$ is straight chain, branching, monocyclic, polycyclic or cross-linked cyclic alkyl group having oxo group or straight chain, branching, monocyclic, polycyclic or cross-linked cyclic alkyl group without oxo group and $Y^-$ is a counter ion, at least one of $R^7$ and $R^8$ having said oxo group.

14. The pattern transfer method as set forth in claim 13, in which said $R^1$ and said $R^2$ form a group having a saturated carbon skeleton.

15. The pattern transfer method as set forth in claim 14, in which said group is oxo substituted alkylene group.

16. The pattern transfer method as set forth in claim 13, in which said $Y^-$ is anion selected from the group consisting of perfluoroalkylsulfonate ions expressed by general formulae [3], alkylsulfonate ions expressed by general formula [4], camphorsulfonate ions, benzensulfonate ions, alkylbenzensulfonate ions, fluorine-substituted benzensulfonate ions, fluorine-substituted alkylbenzensulfonate ions, fluoride ions and halogenide ions

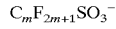

[3]

where m is a positive integer between 1 and 9,

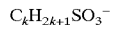

[4]

where k is a positive integer between 1 and 9.

17. The pattern transfer method as set forth in claim 13, further comprising a solvent.

18. The chemically amplified photo-resist as set forth in claim 17, further comprising a cross-linking agent.

* * * * *